United States Patent [19]
Fuglewicz et al.

[11] Patent Number: 5,299,454
[45] Date of Patent: Apr. 5, 1994

[54] CONTINUOUS FOOT-STRIKE MEASURING SYSTEM AND METHOD

[75] Inventors: Daniel P. Fuglewicz, Depew; David A. Schieb; Conrad Sonderegger, both of Tonawanda, all of N.Y.

[73] Assignee: K.K. Holding AG, Winterthur, Switzerland

[21] Appl. No.: 988,699

[22] Filed: Dec. 10, 1992

[51] Int. Cl.$^5$ .......................... A61B 5/11; G01L 5/16
[52] U.S. Cl. ..................... 73/172; 128/779
[58] Field of Search ............... 73/172, 865.09, 862.041; 128/774, 779

[56] References Cited

U.S. PATENT DOCUMENTS

| | | |
|---|---|---|
| 2,653,475 | 9/1953 | Kraus . |
| 3,346,866 | 10/1967 | Bechtel .............................. 73/172 X |
| 3,850,034 | 11/1974 | Tsuchiya et al. ..................... 73/172 |
| 3,894,437 | 7/1975 | Hagy et al. . |
| 4,014,398 | 3/1977 | Gresko ................................ 128/779 |
| 4,122,840 | 10/1978 | Tsuchiya et al. . |
| 4,598,717 | 7/1986 | Pedotti ................................ 128/779 |
| 4,644,801 | 2/1987 | Kustanovich ..................... 73/172 X |
| 4,813,665 | 3/1989 | Carr . |
| 4,814,661 | 3/1989 | Ratzlaff et al. ................... 73/172 X |
| 4,830,021 | 5/1989 | Thornton . |
| 4,858,620 | 8/1989 | Sugarman et al. ............... 73/172 X |
| 4,927,138 | 5/1990 | Ferrari . |
| 4,928,959 | 5/1990 | Bassett et al. . |
| 5,186,062 | 2/1993 | Roost .............................. 128/779 X |

OTHER PUBLICATIONS

Horstmann, G. A., et al, "Special Treadmill for the Investigation of Standing and Walking in Research and Hospital," *Biomedizinische Technik*, 32:250–254, 1987 (German).

Kram, R. A., Powell, A. J., "A Treadmill-mounted Force Platform," *Journal of Applied Physiology*, 67(4):1692–1698, 1989.

Jansen, E. C., et al., "Normal Gait of Young and Old Men and Women," *Acta Orthop, Scand.*, 53: 193–196, 1982.

Martin, M. A., et al, "Ground Reaction Forces and Frontal Plane Hip, Knee and Ankle Angles During Running on a Treadmill," *Biom, XI-B*, vol. 7B:645–649, Human Kinetics Publishers, 1988.

Roemer, R. B., Locascio, J. G., "Rotating Treadmill for the Continuous Measurement of Anterior-Posterior Forces During Walking," *Medical & Biological Engineering & Computing*, 20:519–522, 1982.

Hirokawa, S., et al, "Biofeedback Gait Training System," *Biom, XI-B*, vol. 7B: 1004–1009, 1988.

Kram, R., "A Treadmill Mounted Force Platform," Abstract #295, XII International Congress of Biomechanics Congress Proceedings, University of California, Los Angeles, 1989.

Primary Examiner—Daniel M. Yasich
Attorney, Agent, or Firm—Barnes & Thornburg

[57] ABSTRACT

A foot-strike measuring system and method using a pair of tandem plates each having at least two sensors along the direction of travel for measuring force. By monitoring the signals on the sensors at the adjacent edges and comparing with those on the nonadjacent sensors, the system determines whether one foot is on both plates or one foot is on each plate. This allows collecting and tracking sensor signals for each foot separately. Center of pressure is also calculated using the speed of the treadmill.

12 Claims, 9 Drawing Sheets

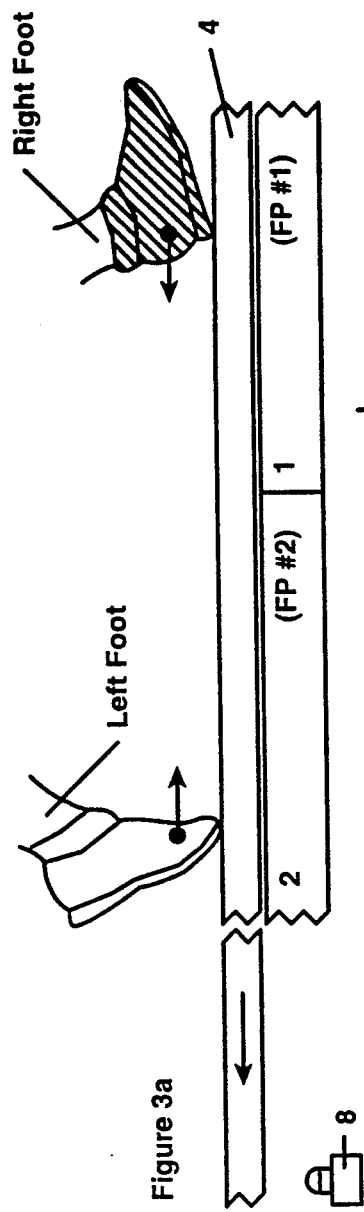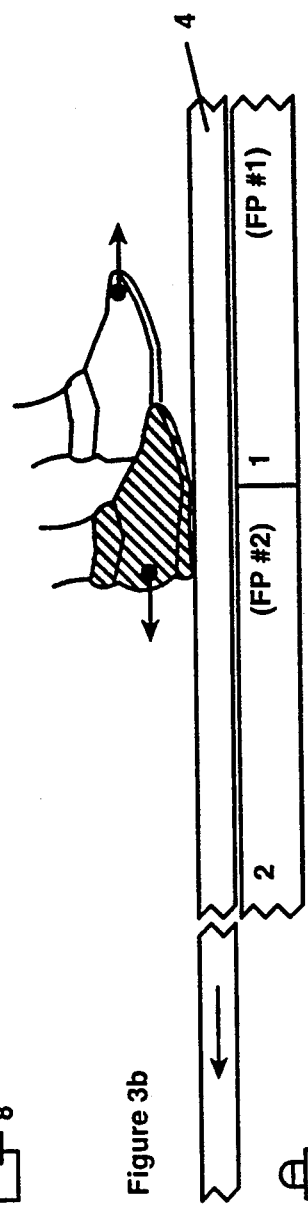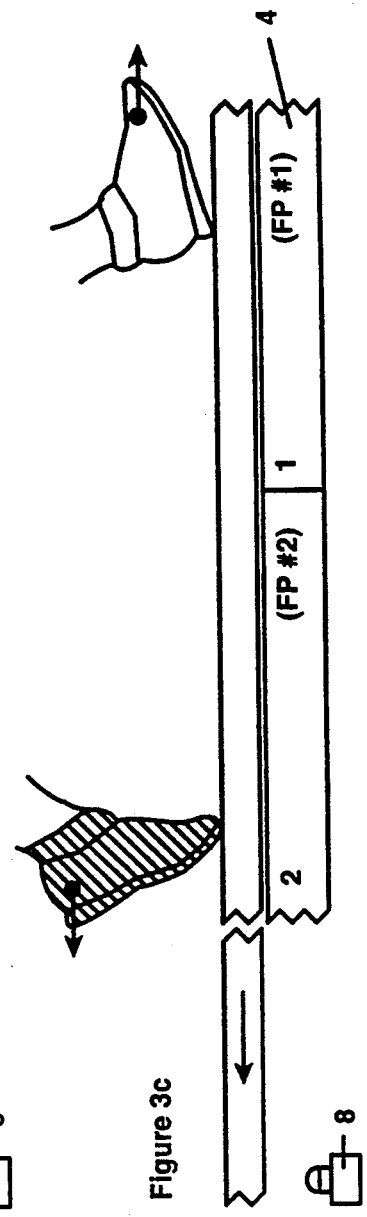

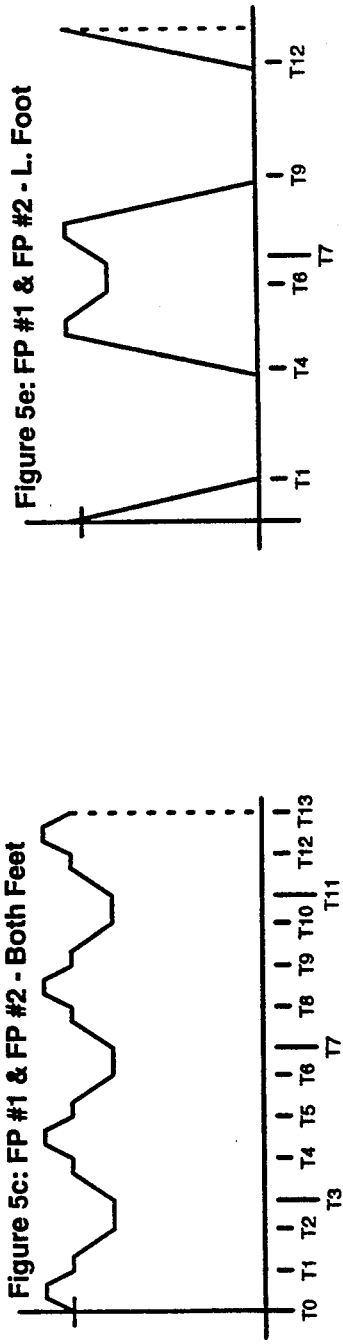
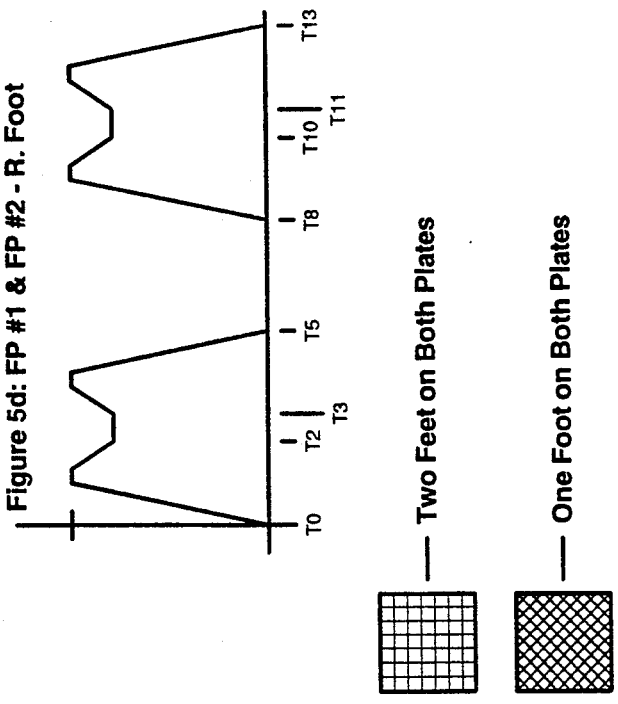
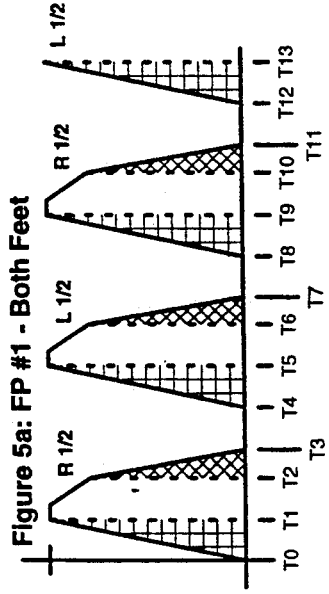
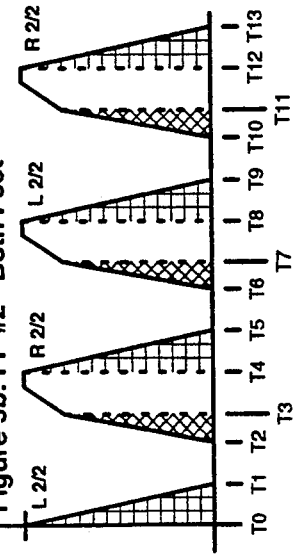

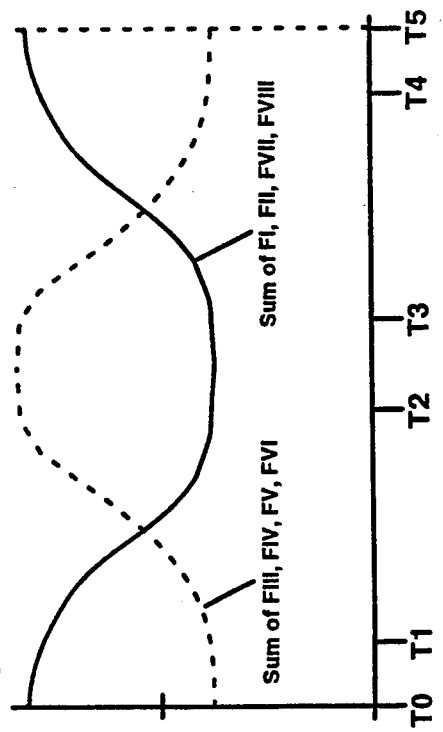
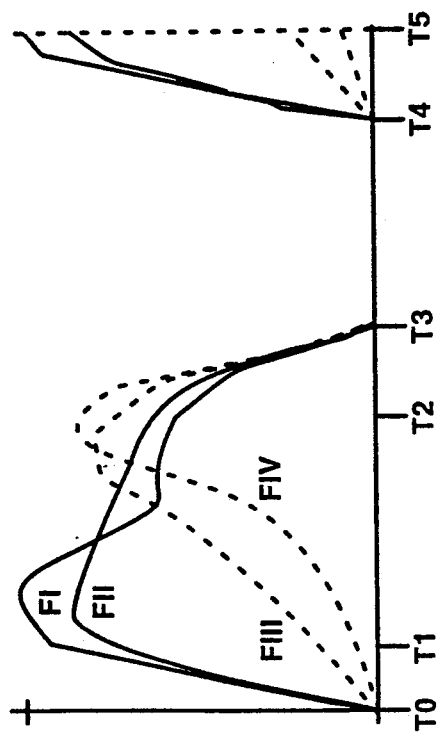
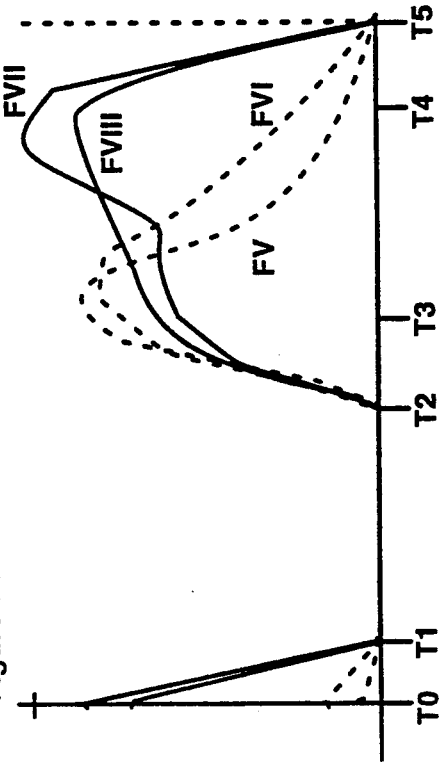

CONTINUOUS FOOT-STRIKE MEASURING SYSTEM AND METHOD

TECHNICAL FIELD

The present invention relates generally to gait and posturographic analysis, and more specifically, to a measuring technique for providing signals for dynamic analysis of gait and balance.

BACKGROUND ART

Gait analysis is an important clinical and research tool for evaluating and diagnosing gait standards and abnormalities. Force plates are generally used to determine the ground reaction forces. Analysis generally include parameters, for example, a time curve of the ground reaction force, time and magnitude of the first and second peak forces, loading and unloading rates, integration of the force-time curve, force vectors display, center of pressure paths, and other parameters relating to individual gait.

One or more force plates are usually positioned along a fixed walkway or path as shown in U.S. Pat. No. 3,894,437. These walkways or paths are typically 1.5 meters wide by 10 meters long. As an alternative to a fixed length path, treadmills have been used to analyze the gait. The treadmills either include a single fixed plate to monitor the forces of both the right and left foot during foot-strikes, or two force plates parallel to the direction of travel are provided under either a single treadmill or belt or a pair of parallel belts. Each force plate monitors the foot-strike of the individual plate.

The short-comings of a single plate is that it cannot distinguish between the right or left foot, or of the simultaneous touching of both feet to the single force plate. Spaced force plates along a walkway often do not capture an unbiased stride, namely, the distance between the right and left foot-strike, or the gait cycles, namely right, left, right. The ability to gather normal gait patterns of a subject is compromised by the need of the subject to concentrate on striking the force plate or plates placed in a specific pattern location. This is known as foot-strike bias. A walkway also does not allow the gait analysis at various fixed, controlled and accurate speeds. Variability in gait parameters result from the difference in walking speeds.

As with the walkway, a single plate treadmill system does not permit distinguishing individual foot-strikes when two feet are on the treadmill simultaneously. Thus single plate treadmills are only accurate for running gait analysis, since in running gait, only one foot contacts at a time. The treadmill that uses two parallel plates also produces an unnatural gait resulting in foot-strike bias.

SUMMARY OF THE INVENTION

Thus, an object of the present invention is to provide a foot-strike measuring system which can be used with a treadmill or walkway and is capable of distinguishing between individual foot-strikes.

Another object of the present invention is to provide a foot-strike measuring system which is free from foot-strike bias.

Another object of the present invention is to provide a foot-strike measuring system which allows for repeated measurements of the complete foot-strike.

These and other objects are achieved by a foot-strike measuring system having first and second plates arranged in tandem with respect to the direction of travel of the subject on the system. First and second sensor systems sense foot strike forces on a respective plate. The system determines from the first and second sensors whether a single foot is on both plates, or one foot is on each of the plates. The signals are processed from the first and second sensor systems as a function of the determination of one foot on both plates or one foot on each of the plates to measure individual foot-strikes. The system for each plate includes at least two transducers or sensors spaced along the direction of travel. The occurrence of a single foot on both plates is determined when the sum of forces on a first pair of transducers, one from each plate adjacent to each other, is greater than the sum of forces on a second pair of transducers, one from each plate and separated by the first pair of transducers. There are two additional transducers on each plate spaced along the direction of travel and spaced transverse to the direction of travel from a respective first transducer.

A center of pressure for each foot-strike is determined from the forces on the first and second pair of sensors on both plates. A treadmill belt is provided above the plates with a sensor for sensing the speed of the belt. The speed is used in determining the center of pressure for each foot-strike. The speed of the treadmill is controlled to maintain the subject substantially centered over the plates along the direction of travel. If needed, the sensors for each plate are individually reset when a force is not sensed by the sensor in a measuring cycle. Signals from the first and second sensor systems are combined when one foot is determined and the signals are separated when one foot on each of the plates is determined.

The method of individually processing signals of consecutive foot-strikes in a two tandem plate system includes determining from first and second systems under the respective plate when the force on the two plates is nearer adjacent or nonadjacent edges of the plates along the direction of travel. Signals from the first and second sensor systems are combined for a single foot-strike when the force is determined to be near the adjacent edges. The signals are segregated as a pair of foot-strikes the force is determined nearer to the nonadjacent edges.

Other objects, advantages and novel features of the present invention will become apparent from the following detailed description of the invention when considered in conjunction with the accompanying drawings.

BRIEF DESCRIPTION OF THE DRAWINGS

FIGS. 3A-3C illustrate the position of a right and left foot of a subject with respect to the force plates of the present invention.

FIGS. 5A and 5B are graphs of the forces measured from the first and second force plates, respectively.

FIG. 5C is a graph of combined signals of FIGS. 5A and 5B.

FIGS. 5D and 5E are recombined graphs of the right foot and left foot, respectively, according to the principles of the present invention.

FIGS. 7A and 7B are graphs of the forces sensed by the four transducers of the first and second plates, respectively.

FIGS. 7C is a graph of the sum of the transducers I, II, VI, VIII and transducers III, IV, V, VI.

BEST MODE FOR CARRYING OUT THE INVENTION

Figure 1A:
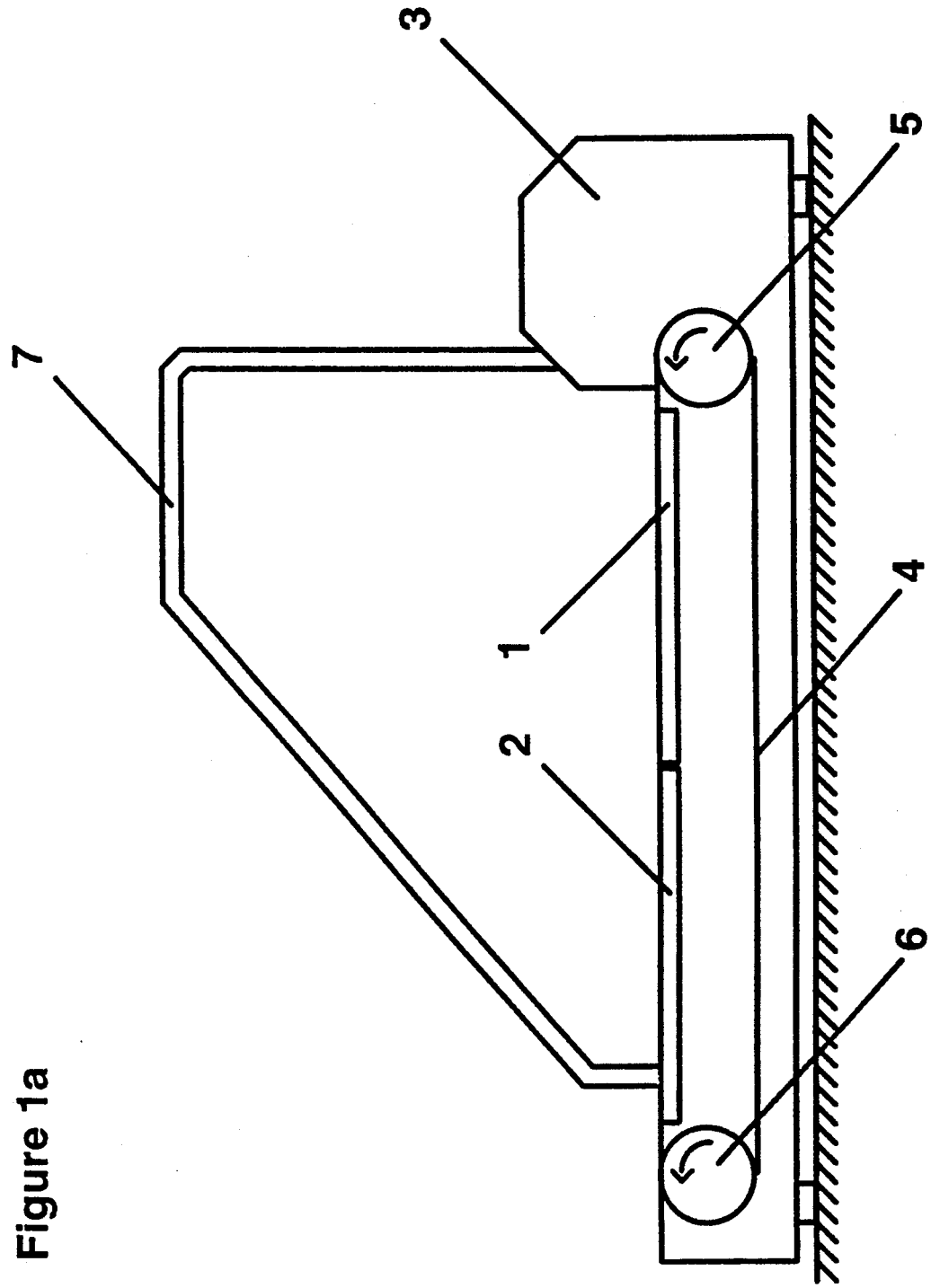
FIGS. 1A and 1B are side and plan views, respectively, of a treadmill incorporating the principles of the present invention.
Figure 1B:
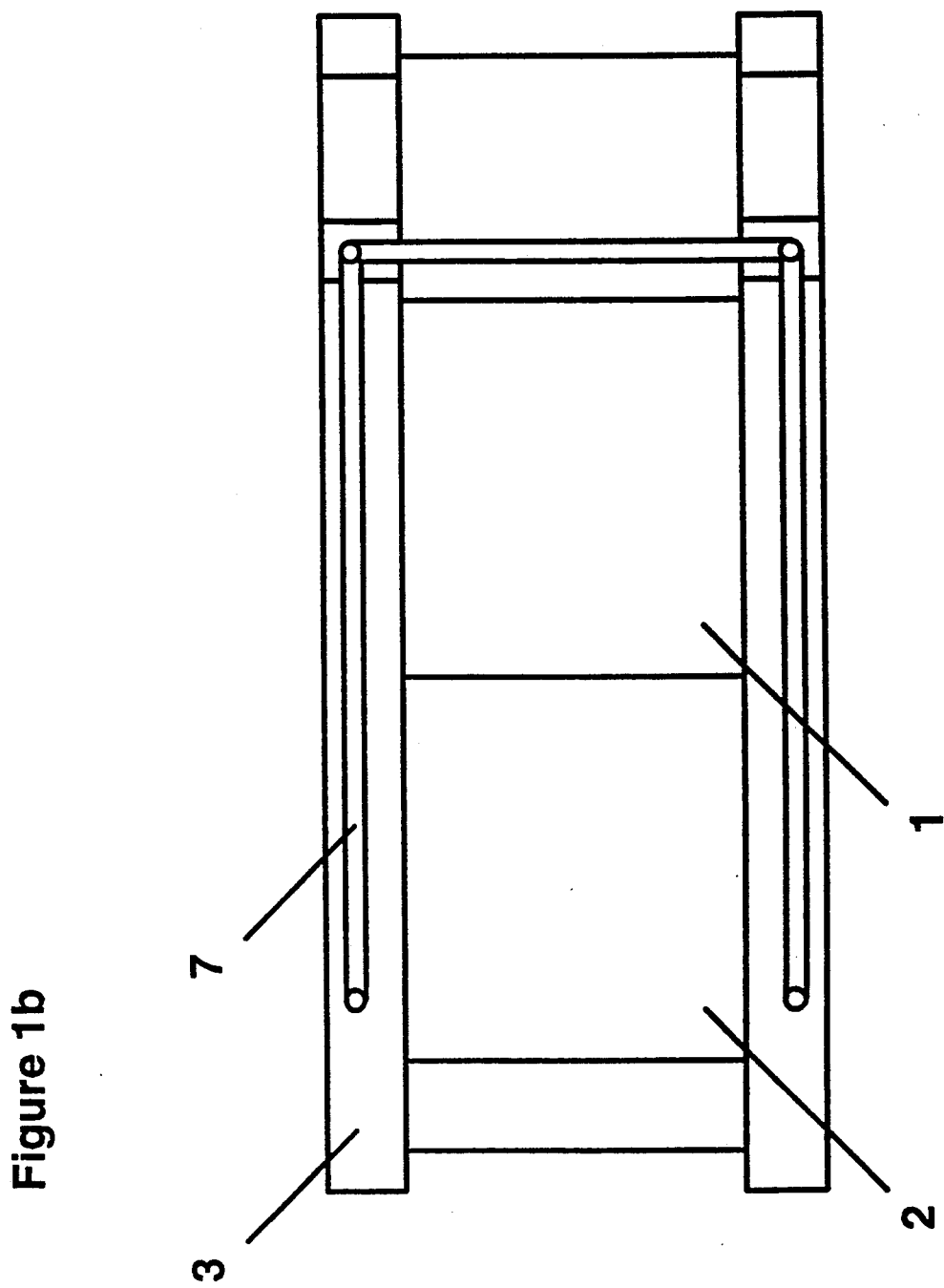
Figure 4B:
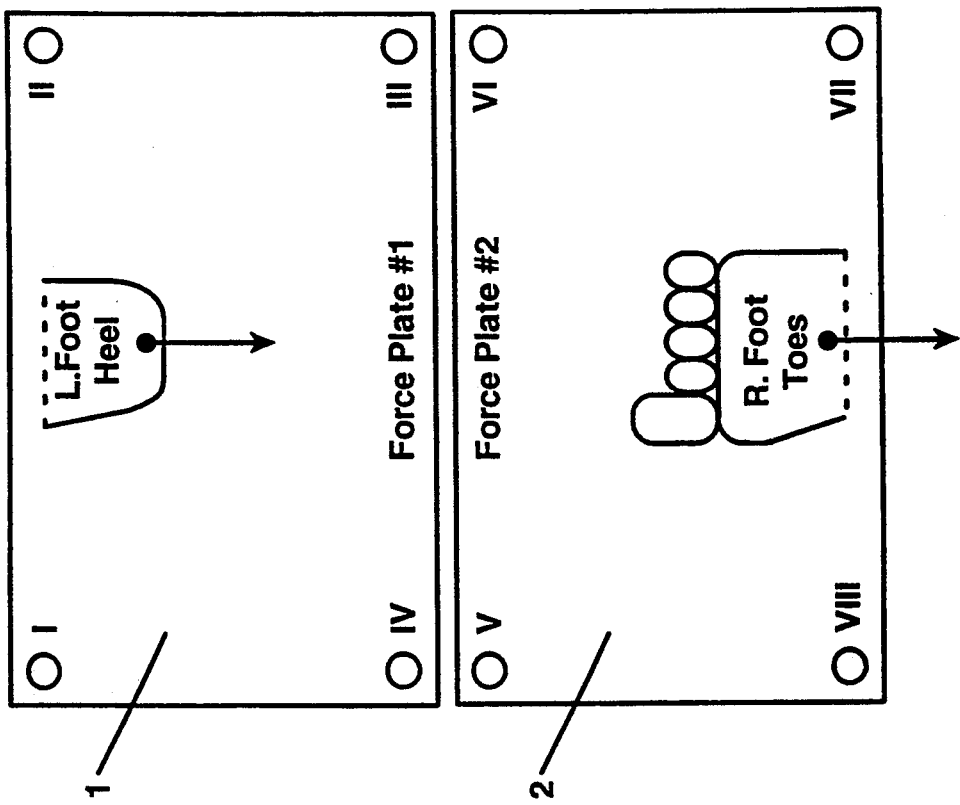
FIGS. 4A and 4B are plan views corresponding to FIGS. 3B and 3C, respectively.

In a first embodiment, tandem force plate treadmill is illustrated in FIGS. 1A and 1B which combines the measuring capabilities of a force plate instrumented walkway and the ease of using treadmill technology to measure ground force reaction forces for gait and posturographic analysis. The pair of force plates 1 and 2 are placed in tandem along the direction of travel under a treadmill belt 4. A pair of rotating drums 5 and 6 are secured to the frame 3 and drive the treadmill belt 4. A handrail 7 is provided on the frame 3. The force plates 1 and 2 include sensor systems sensitive to forces in one or more axes. These sensor systems will be described more specifically with respect to FIGS. 4A and 4B.

As will be discussed below, the configuration of force plates 1 and 2 in tandem in the direction of travel allows the system to distinguish between right and left foot-strikes when a subject is walking on the belt. In that the system is incorporated into a treadmill design, very little space is used and the subject remains at the same relative location while ambulating. Synergistic measurements like oxygen uptake, EKG, EMG, EEG, and kinematic measurements can be obtained conveniently without the limitations of moving instrumentation, panning cameras, or excessive cabling.

Figure 2:
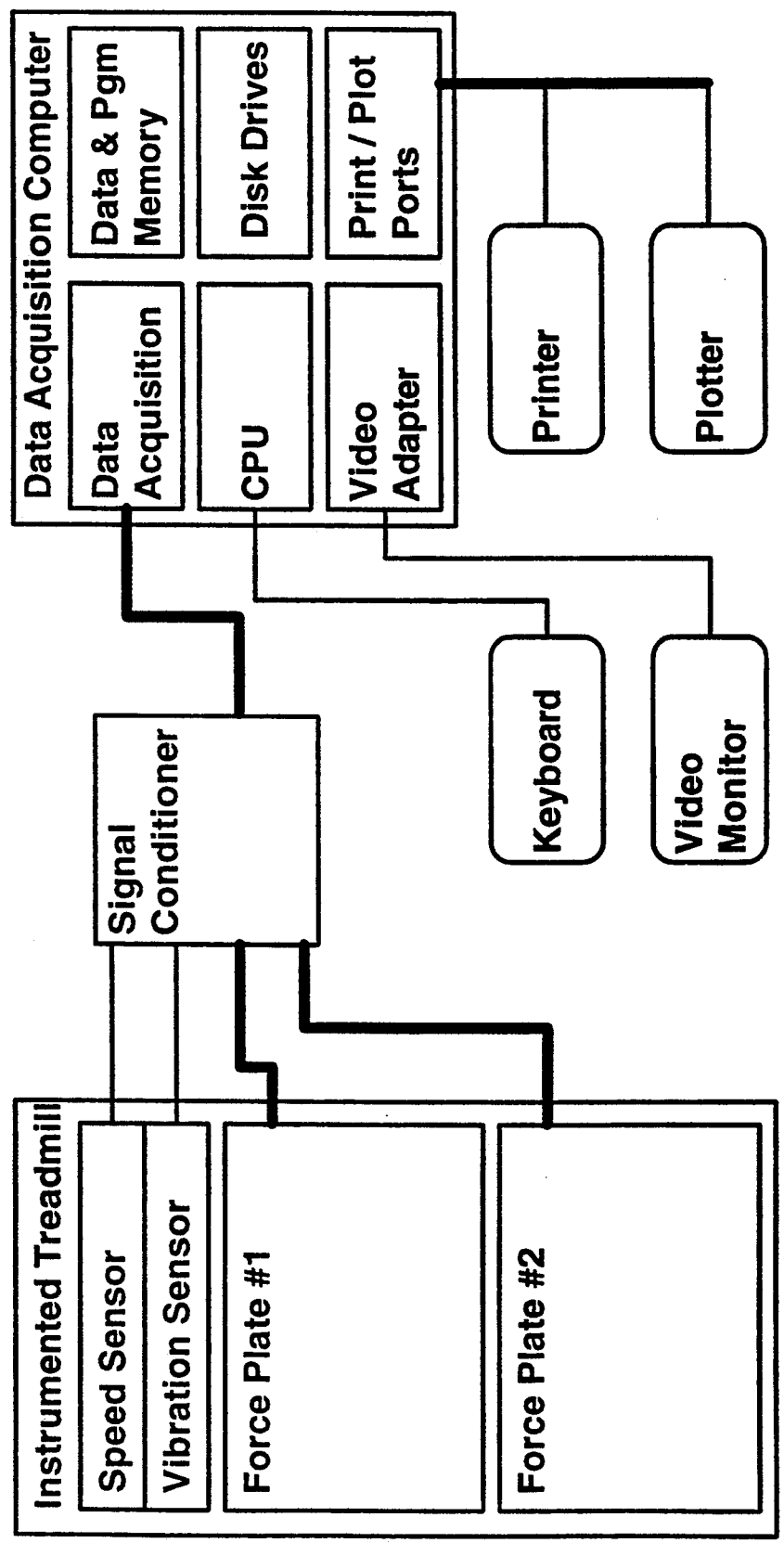
FIG. 2 is a block diagram of a system incorporating the principles of the present invention.

The instrumentation system, as illustrated in FIG. 2, shows the treadmill having force plates 1 and force plates 2 as well as a speed sensor. An optional vibration sensor is also provided. The output from the force plates is provided through signal conditioners, for example, amplification and/or filtering to the data acquisition system. The speed sensor and the vibration sensor are also connected to the data acquisition system. The data acquisition system converts the analog signals to digital signals. Data and program memory, disk drives, video adapter, printer/plotter ports may be provided to drive an appropriate video monitor, printer and plotter, respectively. A keyboard is also provided for input control to the data acquisition computer. The data acquisition computer acquires data, reduces data, displays the forces and associated parameters during data acquisition. The vibration sensor allows the data acquisition system to do additional signal processing to remove system vibratory signals from the signals on the force sensor plate. A speed sensor 8, shown in FIG. 3A, is used in the data acquisition system to calculate the center of pressure as will be discussed below. The belt speed will also give the gait velocity. The rotating drums 5 and 6 are speed controlled. The subject remains substantially centered over the two force plates 1 and 2.

Sources of noise in the signal include high frequency noise from the motor and noise from the belt slipping on the plates. Periodic fixed-frequency noises may be eliminated, by for example, digital filtering.

The general operation of the system will be described with respect to FIGS. 3 and 4 wherein the left foot LF of the subject and the right foot RF of the subject are shown at different positions on the force plates. The arrows indicate the direction of foot motion. In FIG. 3A, the subject's left foot is behind the right foot and is being lifted off from the toe. The right foot, which carries the subject's weight, is over the first force plate P1 and is moved with the belt 4 backwards. Thus in FIG. 3A, only one foot is on each plate. It is considered one end point of the stride. In FIG. 3B, the subject is near mid-support with the right foot being moved by the treadmill belt 4 to be positioned on both force plates 1 and 2. In FIG. 3C, a new step begins with the left foot striking the force plate 1 with the heel down, and the right foot being lifted off from the toe from force plate 2. This is the second end point for the first stride with the heel of the left foot on one force plate 1 and the toe of the right foot on the second force plate 2. The cycle then repeats, beginning as in FIG. 3A, with the left and right foot reversed. Thus, the right foot toe is lifted off the force plate 2 while the left foot travels backwards from force plate 1 to bridge force plate 1 and 2 and finally to traverse completely on force plate 2.

As can be seen from the description of FIGS. 3A through 3C, there are times when the force plates and 2 in combination monitor the signals from a single foot, and other times where they are receiving signals from both feet. Although the signals from the two force plates are separate naturally, the data acquisition system must distinguish between the mid-point position of FIG. 3B when one foot is on both force plates and the position of FIGS. 3A and 3C where one foot is on each of the force plates. As will be described below, the data acquisition system of FIG. 2 is capable of making such a distinction and collects and coordinates the force plate signals for each of the feet individually and continuously over the time scale.

The force plate 1 includes four sensors or transducers, I, II, III and IV, while the second force plate includes the four sensors or transducers V, VI, VII, VIII. Sensors are provided in the four corners of the force plate. Each force plate includes two pairs of sensors spaced along the direction of travel and spaced from each other transverse to the direction of travel. Sensors IV and V and sensors III and VI are sensors at adjacent edges, while sensors I and VIII, and II and VII are considered sensors that are at non-adjacent edges. These will be discussed below with respect to determining whether a single foot is extending across both force plates or two feet are on a respective force plate. The four transducers on one plate measure the force in one or more orthogonal directions or axes. Types of sensing elements that can be used include: piezoelectric, strain gauge, capacitors, pressure, inductive, piezoelectric films or other devices or systems used to measure or derive a force measurement.

A single axis force plate, including force sensors at the four corners is well known in the art. For example, model Z15506 from Kistler. This is a 40×40 centimeter plate. From our complete analysis of the gait and gait related functions, a three-axis force plate may be used, for example, model number 9281B11 from Kistler. This is a 40×60 centimeter multi-component force plate.

A depiction of the signals received on each of the force plates is shown in FIGS. 5A through 5E. The forces on force plate FP1 are shown in FIG. 5A while the forces on force plate FP2 are shown in FIG. 5B.

Figure 4A:
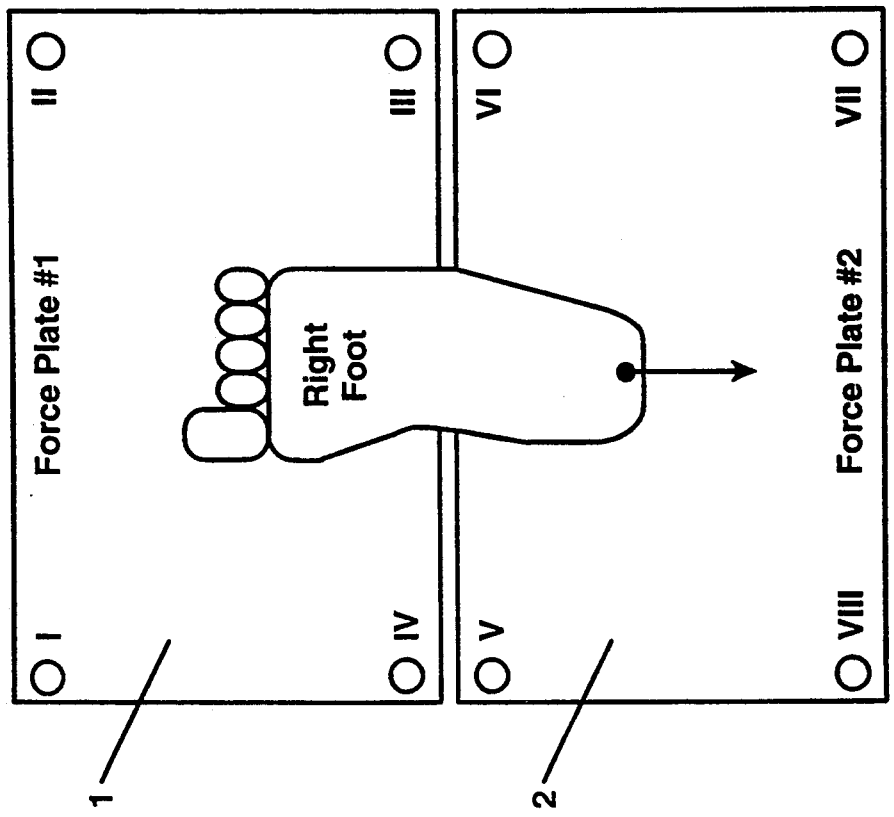

From time T0 through T3, the right foot is on force plate 1. From T0 to T1, the heel of the right foot is on force plate 1 (FIG. 5A) while the toe of the left foot is on force plate 2 (FIG. 5B). This is the condition at FIG. 3A. At T1, the left toe is off force plate 2. At time T2, the right foot is reaching mid-stride or mid-support and begins to overlap from force plate 1 to force plate 2. This period of overlap is from T2 to T3. Time period from T2 to T3 is illustrated in FIG. 3B and 4A. The cross-hatching of each of the figures indicate the time overlaps and the number of feet being supported. From T3 to T5, the right foot is off force plate 1 and is on force plate 2 only. As the subject reaches the end of the first stride illustrated in FIGS. 3C and 4B, the right foot is beginning a lifting of the toe from times T4 to T5 on force plate 2 while the heel of the left foot is striking the force plate 1 as illustrated in times T4 to T5. The cycle then repeats itself for the left and right foot.

The combined signals from force plates 1 and 2 in FIGS. 5A and 5B would result in the signal illustrated in FIG. 5C if a single force plate was used. The object is to separate the right and left foot signals from the two force plates as illustrated in FIGS. 5A and 5B to produce independent signals for the right and left foot. The signal processing according to the present invention produces the independent signals for the right foot in FIG. 5D and for the left foot in 5E. The signals for the right foot in 5D extends from time T0 through T5 using the signals from the first force plate during period T1 through T3, and from the second force plate from T2 through T5. The second right foot is illustrated as occurring from T8 through T13. For the left foot, the signal extends from T4 through T9. The signal from the first force plate 1 is used from time period T4 through T7, and from the second force plate 2 from T6 through T9.

Thus, for example, for time period T2 through T3, the signals from the two force plates are combined or summed since they are from a common right foot. From overlapped period T4 through T5, both force plates have signals, but they are from separate feet and, therefore, they must be segregated. The present system provides a means of determining whether the signals from the two plates are from a common foot and thus summed or a separate foot on each plate using the signals from the force plates alone.

The electronic signal processing system may have a certain amount of signal drift over time. By the use of the tandem force plates 1 and 2, any drift can be nullified during signal gathering. To be more specific, referring to FIGS. 5A and 5B, each force plate has a period in which there is no signal on that force plate. For example, in FIG. 5A, force plate FP1 has no output from T3-T4, T7-T8, and T11-T12. Similarly, force plate FP2 in FIG. 5B monitors no pressure signals from T1-T2, T5-T6, T9-T10. The signal preprocessor or the data acquisition system may sense there is no signal present in one of the force plates and thereby reset the signal conditioning or data acquisition portion of the system.

Figure 6:
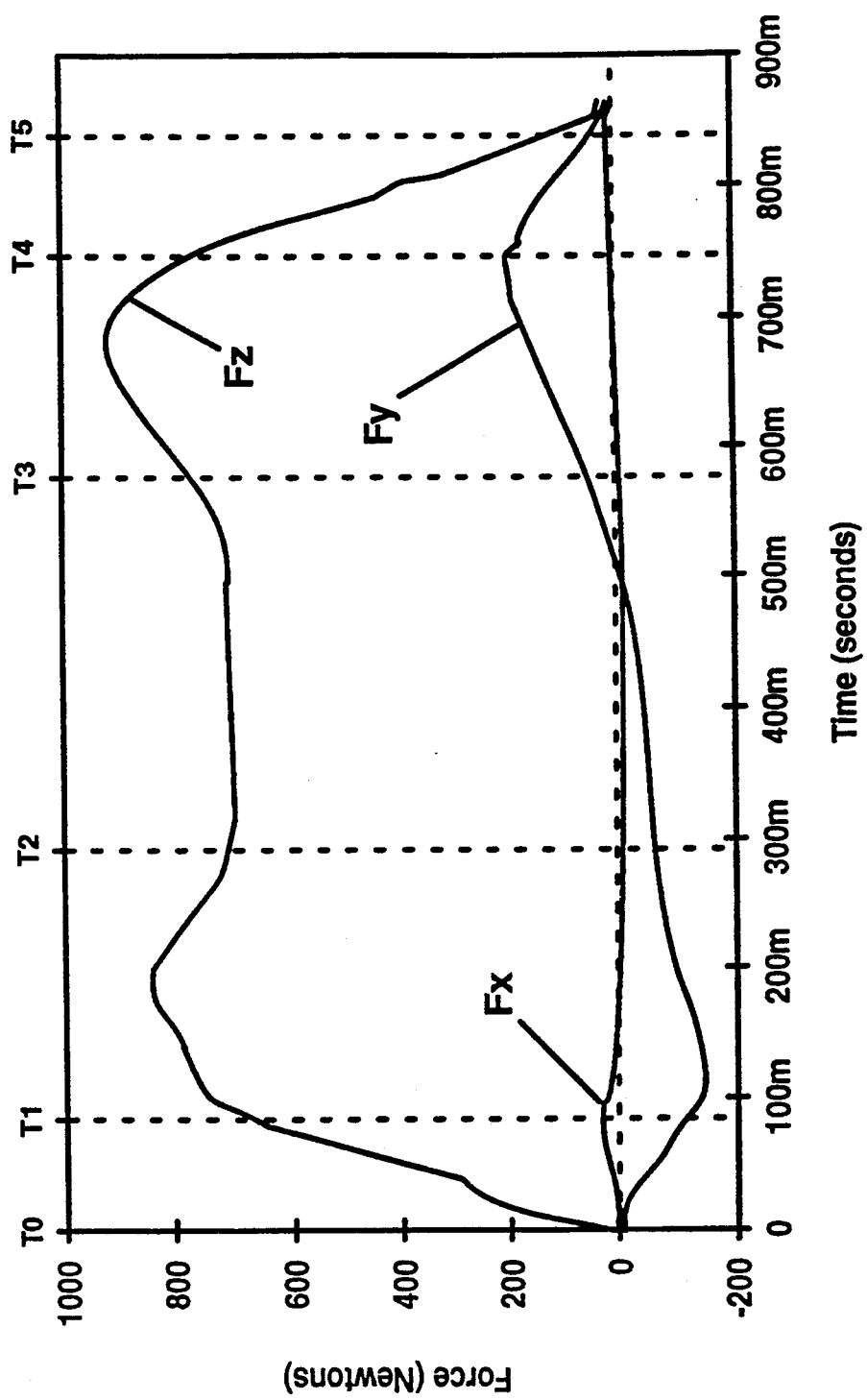
FIG. 6 is the sum of forces in three orthogonal axes of a single foot-strike sensed by the sensors.

The graphs of FIG. 5 are for the Z component only, namely the vertical force applied by the foot-strike. In a multi-axis system, the Y axis is in the direction of travel, the X axis is transverse the direction of travel and the Z axis is a vertical axis. FIG. 6 represents the graph of the three forces for a single foot-strike combining the information from the two force plates. As can be seen, the Y force begins as a negative value working against the axis of motion and diminishes as approaching T3. At mid-support, just prior to T3 when transferring to the second force plate, the Y force becomes a positive value aiding the direction of travel. The X component has a small positive value at the beginning at the end of the stride upon impact and push off while having generally a small negative value during the remainder of the stride indicating a particular foot struck the force plate.

One factor which must be taken into consideration with the Y axis force is the friction between the treadmill belt 4 and force plates 1 and 2. This can be resolved by modeling the friction between the force plate and the treadmill and subtracting this force from the total Y axis forces. Other solutions may also be used.

As can be seen from the composite of FIG. 6 and the graphs of FIG. 5, each tandem plate records approximately half of the full support phase. The first force plate 1 receives approximately the first half of the support phase with an overlap and the second plate receives approximately the second half of the support phase. In order to calculate the total force acting on the force plate, the forces of the sensors in each of the plates are summed together. This yields 100 percent of the total support. It is not important what percentage of force either plate records, since the total force is always 100 percent of the support. Similarly, it is not important if the subject's center of mass is before or after the gap between the two force plates, thereby varying the amount of time there is on one force plate or the other. The measurement is generally not affected by shuffling of feet during the gait. As long as signals can be separated for the right and left foot occurring simultaneously on different force plates, the appropriate measurements can be made.

In order to determine whether a single foot is on both plates or two feet are individually on single plates, the present system monitors the signal from each of the eight sensors I through VIII. The signals on the first four sensors FI through FIV of force plate 1 are shown in FIG. 7A and the signals on the second four sensors of the second force plate FV through FVIII are shown in FIG. 7B. During the normal gait, the strike point is closer to the first two sensors I and II on force plate 1 as illustrated by time period T0 through T1. As the treadmill belt moves backwards, the weight of the foot moves towards the center of the four sensors on the first force plate and ultimately the majority of the weight on the second two sensors III and IV as shown at time T2. As the foot continues to move backward spanning the two plates, the signal on III and IV is diminished by the same amount as the increase on the first two sensors of plate 2, namely V and VI. This phase begins at T2.

By T3, the weight of the foot is shifted to be primarily on the second plate 2 with the forces more towards the sensors V and VI than the rear pair of sensors VII and VIII. The weight of the foot is then centered on the second plate and then shifting to a majority of the weight on the back of plate 2 with a maximum at sensors VII and VIII at time T4. As the foot leaves the plate at T5, the values on all four of the sensors on plate 2 go to zero. It should be noted that the unlettered portions of the graph of FIG. 7A and 7B represent the sensor values for the other foot which in FIG. 7A begins a heel down segment at time T4 and in FIG. 7B begins a toe off segment between T0 and T1.

In order to distinguish between a single foot on both plates and two feet on each of the individual plates, the occurrence of the foot spanning of two plates must be determined with accuracy. Review of graph 7A and graph 7B will indicate that there is a period between T2 and T3 where the sum of the four adjacent sensors FIII, FIV, FV and FVI is greater than the signals on the nonadjacent sensors FI, FII, FVII and FVIII. The sums are illustrated in FIG. 7C. From time T0 through T1, the sum of the signals on the four nonadjacent sensors is greater than the sum of the four adjacent sensors. At T0, one foot is substantially adjacent the first set of sensors FI and FII in a heel down position and the second foot is in a toe off position adjacent the other set of other sensors FVII and FVIII. At T1 the total weight is shifted to the front foot adjacent the first two sensors FI and FII. Between times T2 and T3, the signals at the adjacent sensors FIII, FIV, FV and FVI is greater than the sum at the four non-adjacent sensors FI, FII, FVII and FVIII. From T4 to T5, again the weight shifts from a single foot adjacent the external sensors FVII and FVIII to a shared condition wherein the heel down adjacent the first two sensors FI and FII and a toe up on the last two sensors FVII and FVIII produce a sum greater than the sum on the adjacent sensors FIII, FIV, FV and FVI.

A simple determination can be made that a single foot is on both force plates if the sum of the adjacent sensors FIII through FVI is greater than the sum of the forces on the nonadjacent sensors FI, FII, FVII, FVIII. In other words, the force on the two plates are nearer the adjacent edges. If the sum of the adjacent sensors is less than the sum of the nonadjacent sensors, then one foot is on one of the plates or one foot or an individual foot is each of the plates. In other words, the force on the two plates are nearer the non-adjacent edges, or not near the adjacent edges. This allows segregation of the data from the sensors and the individual plates such that they can be collected, tracked, maintained and displayed for each of the individual foot strikes.

It should be noted that a tandem force plate may be used with active or passive treadmills. In a passive treadmill, the subject rotates the belt during locomotion, where an active treadmill the belt is motor driven. The derivation of forces and the center of pressure as described herein are valid for various speeds of walking and running gaits.

Figure 8:
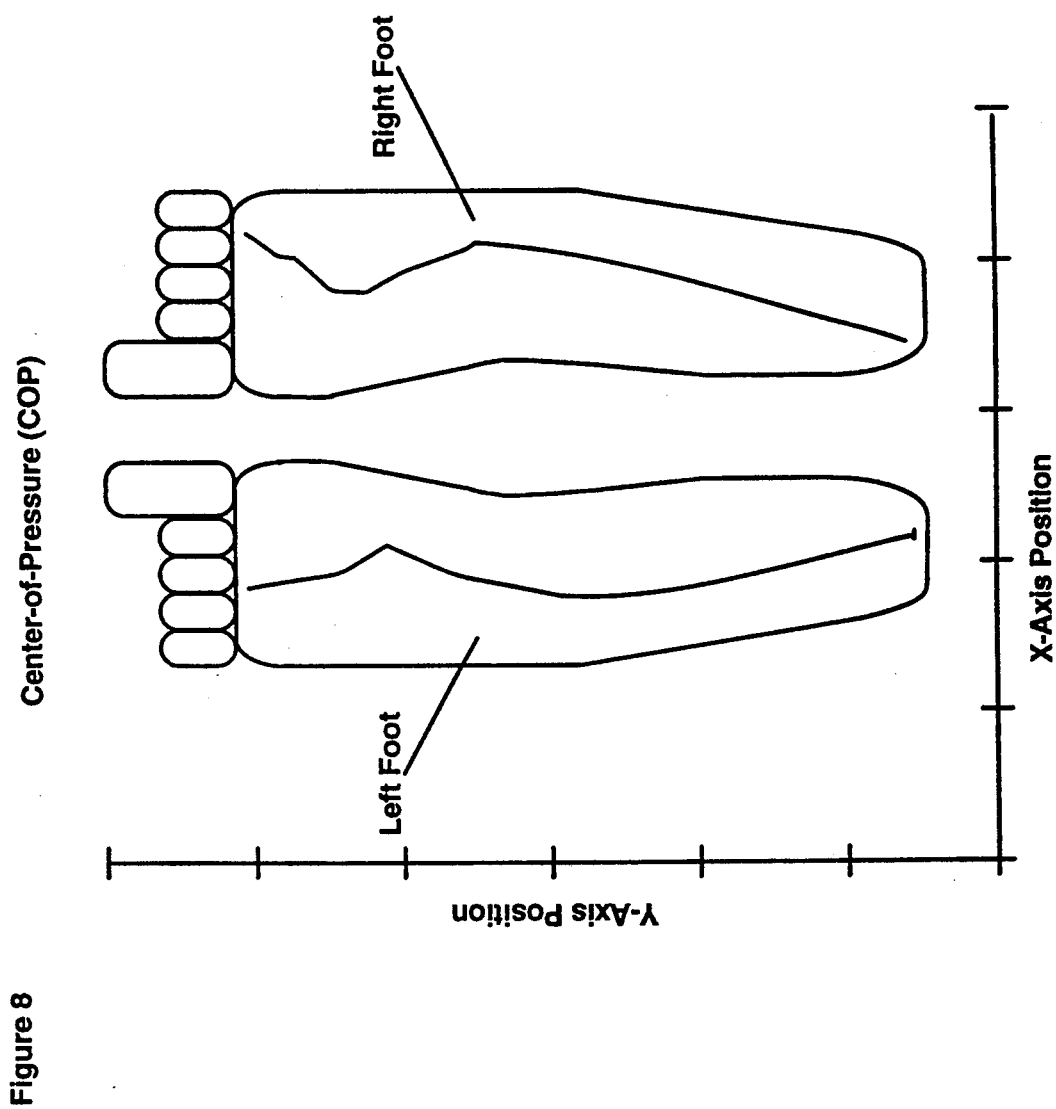
FIG. 8 is a graph of the center of pressure calculated according to the principles of the present invention.

Since the signals for each foot-strike can be isolated and tracked individually even though both feet may be contacting one of the force plates, the calculation of the center of pressure (COP) is determined with the present system using the following formula:

$$A_{x1} = a(F_{II,III} - F_{I,IV})/F_{T1}$$

$$A_{x3} = a(F_{VI,VII} - F_{V,Vm})/F_{T2}$$

$$A_{y1} = b(F_{I,II} - F_{III,IV})/F_{T1}$$

$$A_{y2} = b(F_{V,VI} - F_{VII,VIII})/F_{T2}$$

where $A_{xp}$ = X-axis COP location for force plate P
$A_{yp}$ = Y-axis COP location for force plate P
$F_{Tp}$ = total force all four sensors for force plate P
$F_{mn}$ = sum of transducer forces for transducers "m", "n"
2a = distance between transducers I,II; III,IV; V,VI; VII,VIII
2b = distance between transducers I,IV; II,III; V, VII; VI, VIII For each sampling period, the center of pressure of the individual feet on the tandem force plates can be calculated. The data is then compiled for each of the individual feet. The speed of the treadmill from the speed sensor 8 is subtracted from the movement of the foot on the force plates to produce the actual center of pressure for each of the foot-strikes. FIG. 8 displays the resulting plot of the center of pressure along the left and right foot shown in phantom.

With respect to FIG. 8, the grid is considered to be the sum of the two plates such that the center of pressure is tracked during the total stride.

Although the present invention has been described and illustrated in detail, it is to be clearly understood that the same is by way of illustration and example only. Although four sensors are shown per force plate, additional sensors may be provided. The use of four sensors allows the use of commercially available force plates. Similarly more than two force plates may be used, as one example, four force plates may be used, wherein force plate 1 is divided in half and force plate 2 is divided in half. Similarly, it should be noted that although the invention described is for use with a treadmill, a plurality of tandem force plates may be used on a fixed walkway since the signal processing of the present invention allows the separate processing of the foot-strike of each foot whether it bridges a pair of plates or whether one foot is contacting a respective plate individually. The spirit and scope of the present invention are to be limited only by the terms of the appended claims.

What is claimed is:

1. A foot-strike measuring system comprising:
   a first and a second plate arranged in tandem with respect to the direction of travel of a subject on said system;
   first and second sensor means for sensing forces on a respective plate;
   means for determining from said first and second sensor means whether a single foot is on both plates or one foot is on each plate; and
   processing means for combining signals from said first and second sensor means when one foot on both plates is determined and segregating said signals from said first and second sensor means when one foot on each plate is determined to measure individual foot-strikes.

2. A system according to claim 1, wherein:
   said sensor means each include at least two first transducers spaced along said direction of travel; and
   said determining means determines a single foot on both plates when the sum of forces on a first pair of first transducers, on transducer from each plate and adjacent to each other, is greater than the sum of forces on a second pair of first transducers, one transducer from each plate and separated by said first pair of first transducers.

3. A system according to claim 2, wherein:
   said sensor means each include at least two second transducers spaced along said direction of travel and spaced transverse to said direction of travel from a respective first transducer; and
   said determining means determines a single foot on both plates when the sum of forces on first pairs of first and second transducers, one transducer from each plate and adjacent to each other, is greater than the sum of forces on second pairs of first and second transducers, one transducer from each plate and separated by said first pairs of first and second transducers.

4. A system according to claim 3, wherein said processing means determines a center of pressure for each foot-strike from forces on said first and second pairs of transducers.

5. A system according to claim 1, wherein:
said sensor means each include at least two first transducer spaced along said direction of travel and at least two second transducers spaced along said direction of travel and spaced transverse to said direction of travel from a respective first transducer; and
said processing means determines a center of pressure for each foot-strike from forces on said first and second pairs of transducers.

6. A system according to claim 5, wherein said system includes:
a treadmill belt above said plates;
sensor for sensing the speed of said treadmill belt; and
said processing means determines a center of pressure for each foot-strike from forces on said first and second pairs of transducers and speed of said treadmill belt.

7. A system according to claim 1, including a treadmill belt above said plates.

8. A system according to claim 7, including means for controlling the speed of said treadmill belt to maintain said subject substantially centered over said plates along said direction of travel.

9. A system according to claim 1, including means for resetting each of said sensor means individually when a force is not sensed by the sensor means in a measuring cycle.

10. A system according to claim 1, wherein said sensor means each include at least two first transducers spaced along said direction of travel, and said transducers sense forces along parallel axis.

11. A system according to claim 1, wherein said sensor means each include at least two first transducers spaced along said direction of travel, and each transducer senses forces along one of three orthogonal axes.

12. A method of individually processing signals of consecutive foot-strikes in a system having two force plates in tandem along a direction of travel and a first and a second sensor means for a respective plate, comprising:
determining from said first and second sensor means whether the force on said two plates are nearer adjacent or non-adjacent edges of said plates along said direction of travel; and
combining said signals from said first and second sensor means for a single foot-strike when the force is determined to be nearer to adjacent edges and segregating said signals from said first and second sensor means as a pair of foot-strikes when the force is determined to be near to non-adjacent edges.

* * * * *